United States Patent
Talton (10) Patent No.: US 8,074,906 B2
(45) Date of Patent: Dec. 13, 2011

(54) PROCESS FOR MILLING AND PREPARING POWDERS AND COMPOSITIONS PRODUCED THEREBY

(75) Inventor: James D. Talton, Alachua, FL (US)

(73) Assignee: Nanotherapeutics, Inc., Alachua, FL (US)

( * ) Notice: Subject to any disclaimer, the term of this patent is extended or adjusted under 35 U.S.C. 154(b) by 715 days.

(21) Appl. No.: 11/428,064

(22) Filed: Jun. 30, 2006

(65) Prior Publication Data

US 2008/0029625 A1    Feb. 7, 2008

Related U.S. Application Data

(60) Provisional application No. 60/595,464, filed on Jul. 7, 2005.

(51) Int. Cl.
    *B02C 19/06*    (2006.01)
(52) U.S. Cl. .......................................................... 241/5
(58) Field of Classification Search .................. 241/5
    See application file for complete search history.

(56) References Cited

U.S. PATENT DOCUMENTS

| | | | |
|---|---|---|---|
| 3,897,010 A | | 7/1975 | Weishaupt et al. |
| 4,072,026 A | * | 2/1978 | Oberpriller et al. .............. 62/63 |
| 4,962,893 A | * | 10/1990 | Bochmann et al. .............. 241/5 |
| 5,145,684 A | | 9/1992 | Liversidge et al. |
| 5,354,562 A | | 10/1994 | Platz et al. |
| 5,747,001 A | | 5/1998 | Wiedmann et al. |
| 5,997,848 A | | 12/1999 | Patton et al. |
| 6,406,745 B1 | | 6/2002 | Talton |
| 6,592,903 B2 | | 7/2003 | Ryde et al. |
| 6,595,903 B2 | | 7/2003 | Nerio et al. |
| 6,835,396 B2 | | 12/2004 | Brynjelsen et al. |

FOREIGN PATENT DOCUMENTS

| | | | |
|---|---|---|---|
| GB | 1 594 692 | | 8/1981 |
| GB | 1594692 | * | 8/1981 |
| WO | WO 03/090717 | | 11/2003 |

OTHER PUBLICATIONS

Reply to Written Opinion filed in PCT/US2006/025918 (corresponding to U.S. Appl. No. 11/428,064, filed Jun. 30, 2006), dated May 3, 2007.

International Preliminary Report on Patentability for PCT/US2006/025918 (corresponding to U.S. Appl. No. 11/428,064, filed Jun. 30, 2006) dated Nov. 10, 2006.

International Search Report for PCT/US2006/025918 (corresponding to U.S. Appl. No. 11/428,064, filed Jun. 30, 2006) dated Nov. 10, 2006.

* cited by examiner

*Primary Examiner* — Dana Ross
*Assistant Examiner* — Matthew G Katcoff
(74) *Attorney, Agent, or Firm* — Finnegan, Henderson, Farabow, Garrett & Dunner, LLP (57) ABSTRACT

A method of milling a powder comprising introducing a gas stream containing a cryogenic liquid and a drug carrier gas into a jet mill, and milling a powder with the jet mill in one or more milling passes. A product produced by the method. A milling apparatus comprising a cryogenic gas input system, a powder feeder, a main jet-mill, and at least one output port for collecting the powder.

18 Claims, 2 Drawing Sheets

PROCESS FOR MILLING AND PREPARING POWDERS AND COMPOSITIONS PRODUCED THEREBY

CROSS-REFERENCE TO RELATED APPLICATIONS

The present application claims priority under 35 U.S.C. §119 to U.S. Provisional Patent Application Ser. No. 60/595,464, filed Jul. 7, 2005. The entire contents of the aforementioned application is specifically incorporated herein by reference in its entirety.

FEDERALLY SPONSORED RESEARCH OR DEVELOPMENT

None

BACKGROUND OF THE INVENTION

A. Field of the Invention

The present invention relates to methods for milling and preparing powders, changing the surface properties of a drug particle, and compositions produced thereby. In some embodiments, the process described utilizes jet-milling with a cold stream of gas mixed with air and powders. More specifically the cold gas stream is nitrogen gas mixed with liquid nitrogen, under controlled conditions. The resulting milled particle size can range from less than 200 nanometers to greater than one micrometer, depending on the processing conditions and application. The process described can be used to form a stable powder of a single material, a mixture of materials and/or excipients, as well as modify the surface of particles to improve the dispersion and/or stability of a powder intermediate or final product. The powder compositions produced thereby possess improved properties including, but not limited to, improved flow and dispersibility, stability, resistance to moisture, dissolution/release profiles, and/or bioavailabilies. This process, and the compositions produced, provide significant advantages in the manufacture of pharmaceutical particle delivery systems (PDS), as well as biomedical, diagnostic, and chromatography particulate compositions, where insoluble compounds or sensitive particles, such as proteins or vaccines, are involved that would be degraded using more rigorous, high temperature processing conditions.

B. Description of the Related Art

There has been substantial effort in the last decade to produce drug particles from 100 nanometers to a few microns because of their improved dissolution properties (especially with insoluble drugs) and ability to be absorbed more efficiently. Solid nanoparticle formulations are typically made by wet-milling and subsequent packaging into vials or lyophilization, and may contain large amounts of stabilizers that inhibit aggregation and growth of the particle during drying or storage. Dry-milling of inhaled dry-powder formulations in fluid energy or jet mills, such as for inhaled asthma drugs, has been described, but not under reduced temperature. Use of pure nitrogen gas (non-cryogenic) while jet-milling (U.S. Pat. No. 5,354,562) formulations for inhalation has been shown to reduce insoluble contaminants and inactive fractions in the milled product.

Jet mills are shear or pulverizing machines in which the particles to be milled are accelerated by gas flows and pulverized by collision. There are a number of different types of jet mill designs, such as double counterflow (opposing jet) and spiral (pancake) fluid energy mills. Gas and particle flow may simply be in a spiral fashion, or more intricate in flow pattern, but essentially particles collide against each other or against a collision surface. In counterflow fluid-energy or jet mills, i.e., mills of the character described whereby two particle-entraining streams are directed against one another, the carrying gas may be derived from steel bottles or flasks and is permitted to flow through two venturi nozzles in parallel into the fluid-energy or jet mill chamber, the reduced pressure developed in the venturi nozzle together with increased velocity causes the granular or coarse-particle material to be entrained with high speed along a trajectory counter to the trajectory of the particles of the other stream. When two particle streams moving at high velocity and with high kinetic energy in opposite directions collide, the impact releases this kinetic energy in the form of energy of breakdown whereby the structure of the granules is altered or destroyed. Glancing collisions have a similar effect and are also valuable because they provide a mutual abrasion and rounding of the particles. Air or hot steam are generally used as the milling gas.

Inherently brittle materials that are not affected by moderate heat rise are usually easy to grind under ambient conditions with commercial impact or shear milling equipment. Other less brittle materials may be adequately cooled during grinding by simply passing air or another gas through the grinding mill along with the material to be ground. Many substances, for example, plastic, are difficult or impossible to mill to a fine grain size because of their toughness. However, when such tough materials are exposed to cold, they become brittle, which improves their milling properties. A single propellant gas is cooled before introduction into a jet mills, for example, in U.S. Pat. No. 3,897,010. Cooling the complete propellant gas flow makes it possible to mill materials that could not be milled under normal conditions in jet mills. However, in spite of intensive cooling, and in spite of the self-cooling effect of the cooled propellant gas flow as a result of its expansion, the attainable improvement of the milling properties leaves a great deal to be desired. Although fine grain sizes can be achieved, this is only possible at an excessively high consumption of time and energy. Typically such a gas-cooled system makes economic sense only if the material can be ground at 0° C. or higher, less then that requiring significant cooling equipment and energy consumption.

More resilient or elastic materials and those that are particularly sensitive to heat rise, including many chemicals, pharmaceuticals, food, powder coatings, and organic dyes, can require significant precooling and grinding at 0° C. or below. In this case, the materials require processing in a cryogenic grinding system that's cooled by a cryogen, a refrigerant that produces a low-temperature environment in the system. The low-temperature environment chills the material below the glass-transition point, the temperature at which the material becomes brittle and glass-like, to facilitate grinding in a mill that applies impact or shear, such as a jet-mill.

Cryogenic jet-milling is a well-suited size reduction technique for elastic, resilient materials likely to be damaged or destroyed by heat, i.e. pharmaceuticals. It is known that the rate of dissolution of a particulate drug can increase with increasing surface area, i.e., decreasing particle size. Consequently, methods of making finely divided drugs have been studied and efforts have been made to control the size and size range of drug particles in pharmaceutical compositions. Pharmaceuticals, such as oral nanoparticle delivery systems, may be prepared without using wet processes such as with fine grinding media, as described in U.S. Pat. No. 6,592,903 and related patents, or homogenization, as described in U.S. Pat. No. 6,835,396 and related patents. Using cryogenic conditions while milling for these and other resilient or heat-sensitive materials controls heat build-up, which can protect and enhance final product properties, produce finer particles/improve nanoparticle size yield, and increase the production rate.

Delivery of discrete nanoparticles and microparticles have been investigated for inhalation, nasal, topical, ocular, buccal, and injectable delivery. Pulmonary delivery of low molecular-weight drugs, peptides/proteins, and gene-therapy agents for local or systemic therapies presents unique formulation challenges. Efficient and reproducible drug deposition to central sections of the lung, such as glucocorticoids for asthma therapies, and peripheral sections of the lung for systemic delivery, such as insulin for patients with diabetes, is difficult because of limitations involved in aerosolization, stability, and clearance of micron-sized liquid droplets and powders. Currently available delivery systems for the inhalation of drugs include metered-dose inhalers (MDI's), dry-powder inhalers (DPI's), and nebulizers. Inhaled delivery of small molecule drugs including beta-agonists, such as albuterol, and glucocorticoids, such as budesonide and fluticasone propionate, have been used clinically for decades where small portions (20-200 µg) of the packaged dose are deposited in the desired portions of the lung (typically 5-10%). New non-invasive inhaled therapies being developed, such as peptides and proteins intended for systemic delivery, have distinctive physicochemical properties that further complicate efficient delivery, as well as may require large 'lung-doses' in the order of 2-20 mg, i.e. insulin. Dry-powder formulations of macromolecules are of particular interest for inhaled therapies since their stability is higher in the dry-state. Unfortunately, current formulations and inhalers are inefficient with fine particle doses of 5-20% of total emitted dose and high dose-to-dose variability. Spray-dried insulin particles aerosolized in an active pressured inhaler device, such as described in U.S. Pat. No. 5,997,848 and related patents, are able to provide >50% respirable fraction, although only 5-15% of insulin is absorbed systemically. Improved inhaler devices and particle processing techniques are needed to efficiently deliver therapeutics through the pulmonary route.

Final dosage forms that incorporate drug particle compositions, such as a tablet, inhaled powder, or a solution for injection, typically contain bulking agents and/or surface stabilizers that may be chemically or physically attached on the surface, or more simply physically mixed, to disperse effectively. Oral tablets and capsules, as well as inhaled dry-powders, typically incorporate at least one pharmaceutically acceptable water-soluble or water-dispersible excipient. Common agents include carriers, dispersants, or generally excipients, which require additional mixing to obtain biological activity upon storage and administration of a final dosage form. Because of the inherently high electrostatic forces present in nanoparticles and microparticles, direct mixing with carrier particles, such as in dry-powder inhaled formulations, may be inefficient and result in low quality final products. For this reason, manufacturing of nanometer and micrometer size drug particles that include excipients before the bulk mixing phase to improve the dispersion properties are of great interest to produce an improved final product. An example of a drug particle microencapsulation process is also described in U.S. Pat. No. 6,406,745 which may be used to microencapsulate drug particles efficiently without the use of solvents or high temperatures, which may damage the drug molecule or activity.

Particle formation methods by crystallization, solvent evaporation, and granulation are practiced in the pharmaceutical, biotechnology, and food industry. Particle size is often reduced through secondary processing such as milling, while particle size may be increased through granulation and spray-coating techniques. Unfortunately, for small nanoparticles and microparticles used for inhaled, nasal, injectable, oral, and topical delivery, the resulting particles are highly charged and very cohesive, reducing their manufacturability and delivery efficiency and subsequent therapeutic efficacy. Therefore, what is needed are improved, cost-effective methods for preparing particles that do not suffer these limitations, and that are useful in preparing particles with distinct particle sizes and surface properties to obtain a superior final product.

SUMMARY OF THE INVENTION

It has been discovered that addition of a cold liquid gas, such as liquid nitrogen, to a dry gas, such as nitrogen and/or air, while jet-milling a product, in addition to performing two or more successive batch run milling passes, may be used to produce a dry nanoparticle product at low cost. In one embodiment, the process utilizes a venturi-type nozzle or 'Tee' valve to introduce liquid nitrogen with nitrogen and/or air economically to a jet mill, not requiring cooling of the entire jet-mill gas source. Combinations of dry gases used to eliminate moisture-induced agglomeration, as well as promote brittle fracture of particles upon impaction, have been observed to act synergistically to produce a marked improvement in the particle size reduction efficiency. The nanoparticle dry-powder preparations may be stored and later reconstituted for injection, or delivered orally or by inhalation in example embodiments.

The cryogenic liquid, such as liquid nitrogen, is directly injected in with the gas flow to precool the material before it enters the impact area of the jet mill, as well as maintain cooling in the mill as the material is ground. Liquid nitrogen (from a metal dewar), in one embodiment, which exists at −320° F., undergoes a direct phase change from liquid to vapor. Its large cooling capacity (186 Btu/lb) produces an efficient cooling system upon addition to the gas flow in small ratios.

In another embodiment, the cryogenic milling apparatus is composed of (1) a compressed air and/or nitrogen source, (2) a liquid nitrogen tank (or dewar), (3) a venturi-type nozzle or 'Tee' and related control valves to introduce liquid nitrogen to the gas flow, (4) a hopper and/or cryogenic pre-cooler using a screw feeder, connected to a powder introduction port, (5) the jet-mill, and (6) jet mill discharge, including a cyclone, powder collection, and a baghouse to separate fines from the gas flow. The gas flow is allowed to mix with room air, thus recirculation of the gas is not an object of the present invention.

In another embodiment, particles are made in one or more successive batch milling passes. Unlike slow continuous wet-milling methods with rigid grinding media (U.S. Pat. No. 5,747,001 and related patents), separation of an agent from the grinding media and drying is not required in the present process. Conducting two or more passes, for example, may be used to eliminate small amounts of larger particles observed in a bimodal distribution following a single milling pass. Further particle size reduction, from several microns to well below one micron, may be produced by conducting two or more passes. Samples for particle size characterization and improved in-process batch-to-batch control may be imparted by conducting two or more passes in a batch mode. The milled powder from the collection cup may also be refed into the hopper/front of the mill, essentially making the process continuous.

In one embodiment, the present invention provides a method of milling a powder, comprising: introducing a gas stream comprising cryogenic liquid and a dry carrier gas into a jet mill; and milling a powder with said jet mill in one or more milling passes. In one embodiment, the milling may be conducted as a batch operation, and the milling may include more than one pass done successively. In one embodiment, the gas stream may comprise liquid nitrogen. The powder may comprise one or more disintegrants, dispersion agents, solubilizers, surfactants, sugars, salts, fatty acid permeation enhancers, or drugs. In one embodiment, the milling of said powder may be performed in two or more successive milling passes. In one embodiment, the milling of said powder may comprise a shear mixing or grinding step of said powder. In one embodiment, the powder may comprise particles having diameters from less than about 100 nanometers to greater than about 1 millimeter. In one embodiment, the milling may occur at a temperature of about 20 degrees Celsius or lower. In one embodiment, the milling may occur at a temperature of about −100 degrees Celsius to about 20 degrees Celsius. In one embodiment, the invention also provides a milled powder formed according to the method.

In another embodiment, the invention provides a method of milling a powder, comprising: introducing a gas stream comprising liquid nitrogen and a dry nitrogen gas into a jet mill; and milling a powder comprising particles having a diameter of less than about 100 nanometers to greater than about 1 millimeter in said jet mill in two or more milling passes. In one embodiment, the milling may be conducted as a batch operation, and the milling may include more than one pass done successively.

In yet another embodiment, the invention provides a milling apparatus, comprising: a cryogenic gas input system; a powder feeder; a main jet-mill; and at least one output port from said jet-mill for collecting said powder.

BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The invention is directed to methods of milling/modifying particulate materials, a milling device, and the particulate materials produced thereby. Particulate materials, also designated as "particles", to be produced in accordance with this invention are those in which small nanometer to micrometer size particles are desirable. Such particle compositions include, but are not limited to, drugs or pharmaceuticals for human or animal use, cosmetics, pesticides, herbicides, fungicides, paints and pigments, as well as inert particles for which a small particle is desirable. Examples might include nanoparticles and microparticle forms of antigens, nucleic acids, proteins, or even pharmaceuticals. The possibilities and combinations are numerous.

In general, the setup includes a venturi-type nozzle or 'Tee' valve to introduce cryogenic gas to a jet mill. Combinations of dry gases at cryogenic temperatures (generally below 0° C.) before introduction into the jet mill is used to eliminate moisture-induced agglomeration, as well as promote brittle fracture of particles upon impaction, and has been observed to act synergistically to produce a marked improvement in the particle size reduction efficiency. Cryogenic liquids suitable for use in this method include liquid argon, liquid nitrogen, liquid helium or any other liquified gas having a temperature sufficiently low to produce brittle fracture of particles. The cryogenic liquid also prevents milling losses and thermal damage to the feed material that would otherwise be caused by the volatization or overheating of constituent ingredients. A powder is placed in a temperature controlled vessel, such as a jacketed hopper or a screw-feeder, or is frozen beforehand. The cryogenic liquid and gas inputs are opened and the flow and temperature is set to the desired process conditions. The cryogenic gas input system, for example liquid nitrogen mixed with nitrogen gas, may be connected to a standard commercial jet mill, such as a Trost Gem-T, Trost T-15, Hosikawa Alpine AS Spiral Jet Mill, Sturtevant Micronizer, or similar system as the main carrier gas in a variety of gas input setups. Pre-run setup of the system may include attaching a temperature probe or flowmeter, such as a TSI Model 4040 Flowmeter or similar system, at the gas input or to the top of the cyclone (in place of air relief bag), setting the carrier gas on different input pressures and documenting the gas flow and temperature measurements (CFM). The milling process may be started by turning on the powder feeder and after passing powder through the milling region, the jet-milled powder is collected in the cup or similar receiver unit (typically particles ~1-10 microns) or from the bag above the cyclone (particles <1 micron), depending on the exact run conditions. Ideally, to obtain particles less than 1-10 microns, powder from the cup is run through the jet-mill under similar run conditions multiple times, or passes, to obtain a high yield of the desired particle size. Materials suitable for use in this method can include any materials, including peptides, polypeptides, proteins, polymers, small molecule drugs and non-pharmaceutical materials.

Figure 1:
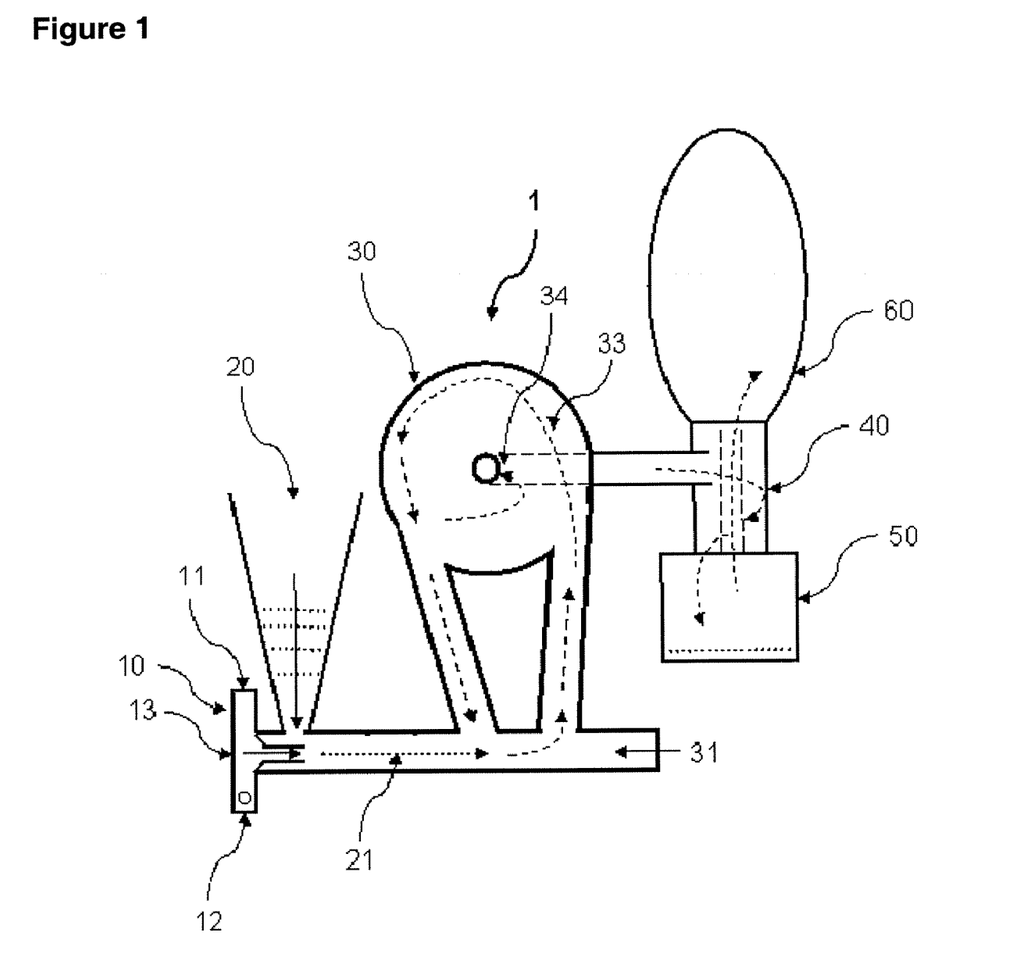
FIG. 1 is a schematic of the milling process.

The modified jet-mill 1, one embodiment shown in FIG. 1, is connected to a cryogenic gas input system 10, powder feeder 20, the main jet-mill 30, the cyclone 40, collection cup 50, and the baghouse 60. The cryogenic gas input system 10 may be composed from hoses from the pressurized carrier gas 11 and cryogenic liquid 12 joined by a venturi-type nozzle or 'Tee' valve 13, which tends to disperse microdroplets of the cryogenic liquid. The cryogenic gas input system is connected to a powder feeder 20 forming a 'freezing region' 21 leading into the main jet-mill 30. The main jet-mill 30 may be formatted from 2 opposing jets (Trost mill) 31 or 3 or more around a circular/spiral milling area (Hosikawa and Sturtevant) (not shown), which is also known as a 'pancake' mill. The circular gas flow forces the largest particles towards the outside perimeter 33 where milling occurs, allowing smaller particles to exit the jet-mill through exit port 34 into the cyclone 40. Larger particles from the cyclone 40 settle into the collection cup 50 by gravity and the smallest particles flow upwards through the cyclone into the baghouse 60. The baghouse 60 may be composed of a fine nylon mesh, as an air relief bag, or HEPA filtration unit to collect particles below 1 micron. The baghouse 60 encompasses a large surface area to address the high gas flow and pressure differential compared to room air where the process is being conducted.

The cryogenic gas input system 10 includes means for directing cryogenic liquid 12 into freezing section 21. Cryogenic liquid 12 flow consists of a spray of liquified gas and/or at least one stream of liquified gas. Freezing section 21 impacts opposing jet 31 and into the main jet-mill 30, depending on the pressure difference between cryogenic gas input system 10 and opposing jet 31. The temperature of the cryogenic gas input system 10, freezing section 21, main jet-mill 30, cyclone 40, collection cup 50, and the baghouse 60 may range from −20° C. to just below room temperature, depending on the processing. When required, relevant internal portions of the apparatus of this invention may be cleaned and sanitized, or sterilized, between each use to assure there is no contamination between batches.

In one embodiment, an oral drug particle is prepared with the present invention. Exemplary pharmaceuticals that would benefit from such drug particle formulations include drugs used in controlled or targeted release, taste-masking, or surface modification prior to tableting or capsule filling.

Several single-component compositions have been described that improve the absorption of drugs, such as (a) the use of bioadhesive polymers or absorption enhancers, which is thought to increase uptake of drugs across cell membranes, or separately (b) formulation into nanoparticles or microparticles which protect the drug from degradation and are absorbed at specific portions of the GI, i.e. Peyer's patches, and are hereby incorporated by reference. Although PDS's such as nanoparticles, microparticles, and microencapsulated particles have shown substantial increases in the absorption of many drugs, such as orally or through the respiratory tract, it is surprising that little effort has been described to improve the bulk properties of the final dosage form, which includes the PDS in combination with binders, bulking agents, dispersing agents, excipients, surface modifiers, and/or enhancers, that may be physically mixed without complicated manufacturing to obtain the optimum biological outcome. Improved compositions and methods of manufacturing such compositions, as well as improved methods of treatment as described herein, have been discovered with improved chemical and biological properties including, but not limited to, excellent powder flow and dispersibility, stability, resistance to moisture, and absorption/release profiles.

It is proposed that PDSs with nanoparticle/microparticle compositions must contain bulking agents and/or surface stabilizers that may be chemically or physically attached on the surface, or more simply physically mixed, to disperse effectively. Oral tablets and capsules, as well as inhaled dry-powders, typically incorporate at least one pharmaceutically acceptable water-soluble or water-dispersible excipient, which in the present invention improves dispersion or dissolution of the final dosage form, i.e. a tablet or inhaled dry powder. Compositions in the present invention include excipients surrounding the PDS in a dry aerosol for inhaled or nasal administration, or in an enteric-coated tablet or capsule that dissolves at the desired region of the gastrointestinal tract upon release, are described thereby presenting the PDS effectively to a biological surface for absorption. Although the use of celluloses in solution with nanoparticles to reduce agglomeration have been described, combining PDS's and dispersants to produce a final dosage form that provides effective dispersion with sustained-release properties have not been reported. Common agents used are carriers or excipients, but have not been adequately described in the art with the delivery of nanoparticles and microparticles of the PDS, which require different manufacturing methods and compositions to take retain significant biological activity upon storage and administration.

Bioavailability is the degree to which a drug becomes available to the target tissue after administration. Many factors can affect bioavailability including the dosage form and various properties, e.g., dissolution rate of the drug. Poor bioavailability is a significant problem encountered in the development of pharmaceutical compositions, particularly those containing an active ingredient that is poorly soluble in water. Poorly water soluble drugs, i.e., those having a solubility less than about 10 mg/ml, tend to be eliminated from the gastrointestinal tract before being absorbed into the circulation. Moreover, poorly water soluble drugs tend to be unsafe for intravenous administration techniques, which are used primarily in conjunction with fully soluble drug substances.

Particularly preferred surface modifiers include polyvinyl pyrrolidone, Pluronic F68 and F108, which are block copolymers of ethylene oxide and propylene oxide, Tetronic 908, which is a tetrafunctional block copolymer derived from sequential addition of ethylene oxide and propylene oxide to ethylenediamine, dextran, lecithin, Aerosol OT, which is a dioctyl ester of sodium sulfosuccinic acid, available from American Cyanamid, Duponol P, which is a sodium lauryl sulfate, available from DuPont, Triton X-200, which is an alkyl aryl polyether sulfonate, available from Rohm and Haas, Tween 80, which is a polyoxyethylene sorbitan fatty acid ester, available from ICI Specialty Chemicals, Carbowax 3350 and 934, which are polyethylene glycols available from Union Carbide. Surface modifiers which have found to be particularly useful include polyvinylpyrrolidone, Pluronic F-68, and lecithin.

Representative polymers that can be used include hydrophilic and hydrophobic polymers, such as those containing carboxylic groups, including polyacrylic acid. In one embodiment, polymers include polyanhydrides, poly(hydroxy acids), and polyesters, such as polylactides, polyglycolides, and blends or copolymers of each, that are currently used in injectable sustained-release systems. Representative bioerodible poly(hydroxy acids) and copolymers thereof which can be used include poly(lactic acid), poly(glycolic acid), poly(hydroxy-butyric acid), poly(hydroxyvaleric acid), poly(caprolactone), poly(lactide-co-caprolactone), and poly(lactide-co-glycolide). Polymers containing labile bonds, such as polyanhydrides and polyorthoesters, can be used optionally in a modified form with reduced hydrolytic reactivity. Positively charged hydrogels, such as chitosan, and thermoplastic polymers, such as polystyrene also can be used.

Specifically, hydrogels or other swelling polymers are incorporated in small amounts in the bulk so as not to make ingestion of the dosage form difficult (for example, less than approximately 23 mm long and less than 11 mm wide for an oval or capsule-shaped tablet). On ingestion, or upon release of the bulk after disintegration from an enteric-coated capsule, they rapidly swell or unfold to a size that precludes passage through the pylorus until after drug release has progressed to a required degree. Gradual erosion of the system or its release of smaller particles in the PDS enables it to leave the stomach or upper regions of the GI in a controlled fashion. Polymers and other materials that swell upon hydration in the GI or the nasal cavity, for example, and increase the local residence time also may be used to improve patient-to-patient variability and improve absorption properties.

Representative natural polymers that also can be used include proteins, such as zein, modified zein, casein, gelatin, gluten, serum albumin, or collagen, and polysaccharides such as dextrans, polyhyaluronic acid and alginic acid. Representative synthetic polymers include polyphosphazenes, polyamides, polycarbonates, polyacrylamides, polysiloxanes, polyurethanes and copolymers thereof. Celluloses also can be used. As defined herein the term "celluloses" includes naturally occurring and synthetic celluloses, such as alkyl celluloses, cellulose ethers, cellulose esters, hydroxyalkyl celluloses and nitrocelluloses. Exemplary celluloses include ethyl cellulose, methyl cellulose, carboxymethyl cellulose, hydroxymethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, cellulose triacetate and cellulose sulfate sodium salt.

Polymers of acrylic and methacrylic acids or esters and copolymers thereof can be used. Representative polymers which can be used include poly(methyl methacrylate), poly (ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other polymers which can be used include polyalkylenes such as polyethylene and polypropylene; polyarylalkylenes such as polystyrene; poly(alkylene glycols), such as poly(ethylene glycol); poly(alkylene oxides), such as poly(ethylene oxide); and poly(alkylene terephthalates), such as poly(ethylene terephthalate). Additionally, polyvinyl polymers can be used, which, as defined herein includes polyvinyl alcohols, polyvinyl ethers, polyvinyl esters and polyvinyl halides. Exemplary polyvinyl polymers include poly(vinyl acetate), polyvinyl phenol and polyvinylpyrrolidone.

Water soluble polymers can be used. Representative examples of suitable water soluble polymers include polyvinyl alcohol, polyvinylpyrrolidone, methyl cellulose, hydroxypropyl cellulose, hydroxypropylmethyl cellulose and polyethylene glycol, copolymers of acrylic and methacrylic acid esters, and mixtures thereof. Water insoluble polymers also can be used. Representative examples of suitable water insoluble polymers include ethylcellulose, cellulose acetate, cellulose propionate (lower, medium or -higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride), polyurethanes, and mixtures thereof.

In one embodiment, a water insoluble polymer and a water-soluble polymer are used together, such as in a mixture. Such mixtures are useful in controlled drug release formulations, wherein the release rate can be controlled by varying the ratio of water-soluble polymer to water insoluble polymer. These mixtures are useful, for example, when formed into PDS, such as those in one embodiment having a diameter between less than about 1 μm and about 1 mm, and in another embodiment between about 400 nm and 10 μm, for oral administration and controlled release of drug.

Polymers that alter viscosity as a function of temperature or shear or other physical forces also may be used. Poly(oxyalkylene) polymers and copolymers such as poly(ethylene oxide)-poly(propylene oxide) (PEO-PPO), known also as Poloxamer, or poly(ethylene oxide)-poly(butylene oxide) (PEO-PBO) copolymers, and copolymers and blends of these polymers with polymers such as poly(alpha-hydroxy acids), including but not limited to lactic, glycolic and hydroxybutyric acids, polycaprolactones, and polyvalerolactones, can be synthesized or commercially obtained.

Polyoxyalkylene copolymers are sold, for example, by BASF under the tradename PLURONICS™. These materials are applied as viscous solutions at room temperature or lower which solidify at the higher body temperature. Other materials with this behavior can be utilized as described herein. These include KLUCEL™ (hydroxypropyl cellulose), and purified xanthum and guar gums.

Other suitable polymers are polymeric lacquer substances based on acrylates and/or methacrylates, commonly called EUDRAGIT™ polymers (sold by Rohm America, Inc.). Specific EUDRAGIT™ polymers can be selected having various permeability and water solubility, which properties can be pH dependent or pH independent. For example, EUDRAGIT™ RL and EUDRAGIT™ RS are acrylic resins comprising copolymers of acrylic and methacrylic acid esters with a low content of quaternary ammonium groups, which are present as salts and give rise to the permeability of the lacquer films, wherein EUDRAGIT™ RL is freely permeable and EUDRAGIT™ RS is slightly permeable, independent of pH. In contrast, the permeability of EUDRAGIT™ L is pH dependent. EUDRAGIT™ L is an anionic polymer synthesized from methacrylic acid and methacrylic acid methyl ester. It is insoluble in acids and pure water, but becomes increasingly soluble in a neutral to weakly alkaline solution by forming salts with alkalis. Above pH 5.0, the polymer becomes increasingly permeable.

In one embodiment, biodegradable polymers of the present invention with low water solubility or which are water-insoluble, include aliphatic polyesters, e.g., homopolymers or copolymers synthesized from one or more kinds of α-hydroxycarboxylic acids (e.g., glycolic acid, lactic acid, 2-hydroxybutyric acid, valinic acid, leucic acid, etc.), hydroxydicarboxylic acids (e.g., malic acid, etc.), hydroxytricarboxylic acids (e.g., citric acid, etc.), or their mixtures; poly-α-cyanoacrylic esters, e.g., poly(methyl α-cyanoacrylate), poly(ethyl α-cyanoacrylate), poly(butyl α-cyanoacrylate), etc.; and amino acid polymers, e.g., poly(γ-benzyl-L-glutamate) etc., or their mixtures. The mode of polymerization for these biodegradable polymers may be any of random, block or graft polymerizations technique.

In one embodiment, the biodegradable polymers are aliphatic polyesters, e.g., homopolymers or copolymers synthesized from one or more kinds of α-hydroxycarboxylic acids (e.g., glycolic acid, lactic acid, 2-hydroxybutyric acid, etc.), hydroxydicarboxylic acids (e.g., malic acid, etc.), and hydroxytricarboxylic acids (e.g., citric acid, etc.), or their mixtures, and so on.

In one embodiment, among the above-mentioned aliphatic polyesters, the homopolymers and copolymers synthesized from one or more kinds of the α-hydroxycarboxylic acids are preferable in view of biodegradability and biocompatibility. In yet another embodiment, the aliphatic polyesters are copolymers synthesized from two or more kinds of the α-hydroxycarboxylic acids. Furthermore, these copolymers can be used as mixtures with, for example, polyethylene glycols (PEGs).

When the α-hydroxycarboxylic acids are chiral compounds they may be composed of pure D- or L-configuration, a racemic mixture, or varying ratios of D- and L- to impart the desired properties. In one embodiment, the ratio of the D-/L-configuration (mol %) is in the range of about 75/25 to about 25/75. In another embodiment, a hydroxycarboxylic acid wherein the ratio of the D-/L-configuration (mol %) is in the range of about 60/40 to about 30/70.

An example of the above mentioned α-hydroxycarboxylic acid polymer is a lactic acid polymer (hereinafter sometimes referred to as "polylactic acid"). The α-hydroxycarboxylic acid copolymer includes copolymers of glycolic acid with the other α-hydroxycarboxylic acids such as lactic acid and 2-hydroxybutyric acid. In another embodiment, the α-hydroxycarboxylic acid copolymers are lactic acid-glycolic acid copolymer and 2-hydroxybutyric acid-glycolic acid copolymer. In yet another embodiment, the α-hydroxycarboxylic acid copolymer is a lactic acid-glycolic acid copolymer.

The polylactic acid in one embodiment has the weight average molecular weight, as defined below, of about 1,000 to about 100,000. In another embodiment, the polylactic acid has the weight average molecular weight of about 2,000 to about 80,000. In another embodiment, the polylactic acid has a weight average molecular weight of about 3,000 to about 60,000. The dispersity (weight average molecular weight/number average molecular weight) of polylactic acid in one embodiment is in the range of about 0.2 to about 4.0, and in another embodiment, in the range of about 0.5 to about 3.5.

The compositional ratio (lactic acid/glycolic acid, mol %) in the lactic acid-glycolic acid copolymer is about 100/0 (homopolymer) to about 0/100, in one embodiment about 90/10 to about 85/15, and in another embodiment about 75/25 to 25/75, and most in yet another embodiment about 60/40 to about 40/60. The weight average molecular weight of the lactic acid-glycolic acid copolymer in one embodiment is about 1,000 to about 20,000, and in another embodiment about 4,000 to about 15,000. The dispersity (weight average molecular weight/number average molecular weight) of the lactic acid-glycolic acid copolymer in one embodiment is about 0.2 to about 4.0, and in another embodiment about 0.5 to about 3.5. The typical example is a mixture of a lactic acid-glycolic acid copolymer wherein the compositional ratio of the lactic acid/glycolic acid (mol %) is about 50/50 and the weight average molecular weight is about 6,000. Another example is lactic acid-glycolic acid copolymer wherein the compositional ratio of the lactic acid/glycolic acid (mol %) is about 50/50 and the weight average molecular weight is about 4,000. In one embodiment, the weight ratio of the mixture is about 25/75 to about 75/25.

The terms "weight average molecular weight" and "number average molecular weight" as used in this specification mean the polystyrene equivalent average molecular weight and number average molecular weight of a sample as determined by gel permeation chromatography (GPC) using 9 polystyrene standards having the weight average molecular weights of 120,000, 52,000, 22,000, 9,200, 5,050, 2,950, 1,050, 580 and 162. These determinations can be made using GPC Column Millenium Stryragel HE 4E (Waters), an HP 1047A refractive index detector (Hewlett Packard), and THF as the mobile phase.

Useful formulations for delivery of drugs typically include carriers such as sugars, salts, starches, celluloses, or other bulking agents. Suitable carriers include, but are not limited to: water, alcohols, salts, gums, vegetable oils, polyethylene glycols, gelatin, carbohydrates such as lactose, amylose or starch, magnesium stearate, talc, silicic acid, viscous paraffin, fatty acid esters, celluloses, polyvinyl pyrrolidone, etc. These preparations can be sterilized and, if desired, mixed with auxiliary agents, such as: lubricants, preservatives, stabilizers, wetting agents, emulsifiers, salts for influencing osmotic pressure, buffers, coloring agents, flavoring agents, and/or aromatic substances.

Oral dosage form compositions in accordance with this invention can also be formulated to additionally contain conventional additives or supplementary ingredients, in the usual amounts for such materials. By way of illustration, such additives or supplements include thickening agents, such as silicic acid (for instance, the trademark designating AEROSIL products); bentonites; colloidal clay; carboxymethyl celluloses; modified montmorillonites, such as alkyl ammonium salts of montmorillonites (for instance, the commercial products known as "BENTONE"); organic thickening and structure-forming agents, such as saturated higher fatty acids and alcohols containing from 12 to 20 carbon atoms (for instance, stearic or palmitic acids, or stearic or cetyl alcohols); waxes; monoglycerides of saturated or unsaturated high fatty acids such as stearic acid, palmitic acid or oleic acid; gelling agents, such as aluminum stearate; dispersing agents, such as ionic, non-ionic or cationic surfactants; emulsifying agents, such as lecithin, and so forth.

The compositions of this invention can also contain pharmaceutically acceptable adjuvants, such as binders or lubricants for tabletting, stabilizing agents, antioxidants, flowing agents (to enhance pourability or flowability during processing), preservatives, flavoring agents, coloring agents and buffering agents. Any of these can be selected from among materials may be used in varying amounts.

For non-parenteral applications, particularly suitable dosage forms are tablets, capsules, inhaled powders, and nasally-delivered powders. Transdermal/intradermal, sublingual, and buccal forms may also be used. Biphasic or controlled-release compositions can be formulated, in which the active components are protected with differentially degradable coatings, e.g., by microencapsulation, multiple coatings, etc. It is also possible to freeze-dry compositions and use the lyophilizates for the preparation of products for administration.

Useful surface stabilizers, which are described in U.S. Pat. No. 5,145,684 to Liversidge, are believed to include those that physically adhere to the surface of the active agent but do not chemically bond to or interact with the PDS. The surface stabilizer may be physically mixed and/or adsorbed on the surface of the PDS in an amount sufficient to maintain an effective average particle size for the PDS. Furthermore, the physically mixed and/or adsorbed molecules of the surface stabilizer are essentially free of intermolecular cross-linkages. Two or more surface stabilizers can be employed in the compositions and methods of the invention.

In one embodiment, suitable surface stabilizers can be selected from organic and inorganic pharmaceutical excipients. Such excipients include various polymers, low molecular weight oligomers, natural products, and surfactants. In another embodiment, the surface stabilizers include nonionic and ionic surfactants.

Representative examples of surface stabilizers include gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters (e.g., the commercially available Tweens® such as e.g., Tween 20® and Tween 80® (ICI Speciality Chemicals)), polyethylene glycols (e.g., Carbowaxs 3550® and 934® (Union Carbide)), polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminium silicate, triethanolamine, polyvinyl alcohol (PVA), polyvinylpyrrolidone (PVP), 4-(1,1,3,3-tetramethylbutyl)-phenol polymer with ethylene oxide and formaldehyde (also known as tyloxapol, superione, and triton), poloxamers (e.g., Pluronics F68® and F108®, which are block copolymers of ethylene oxide and propylene oxide), poloxamines (e.g., Tetronic 908®, also known as Poloxamine 908®, which is a tetrafunctional block copolymer derived from sequential addition of propylene oxide and ethylene oxide to ethylenediamine (BASF Wyandotte Corporation, Parsippany, N.J.)), Tetronic 1508® (T-1508) (BASF Wyandotte Corporation), dialkylesters of sodium sulfosuccinic acid (e.g., Aerosol OT®, which is a dioctyl ester of sodium sulfosuccinic acid (American Cyanamid)), Duponol P®, which is a sodium lauryl sulfate (DuPont), Tritons X-200®, which is an alkyl aryl polyether sulfonate (Rohm and Haas), Crodestas F-110®, which is a mixture of sucrose stearate and sucrose distearate (Croda Inc.), p-isononylphenoxypoly(glycidol), also known as Olin-IOG® or Surfactant 10-G® (Olin Chemicals, Stamford, Conn.), Crodestas SL-40® (Croda, Inc.), and $SA_9OHCO$, which is $C_{18}H_{37}CH_2(CON(CH_3)-CH_2(CHOH)_4(CH_2OH)_2$ (Eastman Kodak Co.), decanoyl-N-methylglucamide, n-decyl β-D-glucopyranoside, n-decyl β-D-maltopyranoside, n-dodecyl β-D-glucopyranoside, n-dodecyl β-D-maltoside, heptanoyl-N-methylglucamide, n-heptyl β-D-glucopyranoside, n-heptyl β-D-thioglucoside, n-hexyl β-D-glucopyranoside, nonanoyl-N-methylglucamide, n-noyl β-D-glucopyranoside, octanoyl-N-methylglucamide, n-octyl-β-D-glucopyranoside, octyl β-D-thioglucopyranoside, and the like.

Other useful cationic stabilizers include, but are not limited to, cationic lipids, sulfonium, phosphonium, and quarternary ammonium compounds, such as stearyltrimethylammonium chloride, benzyl-di(2-chloroethyl)ethylammonium bromide, coconut trimethyl ammonium chloride or bromide, coconut methyl dihydroxyethyl ammonium chloride or bromide, decyl triethyl ammonium chloride, decyl dimethyl hydroxyethyl ammonium chloride or bromide, $C_{12-15}$ dimethyl hydroxyethyl ammonium chloride or bromide, coconut dimethyl hydroxyethyl ammonium chloride or bromide, myristyl trimethyl ammonium methyl sulphate, lauryl dimethyl benzyl ammonium chloride or bromide, lauryl dimethyl (ethenoxy)$_4$ ammonium chloride or bromide, N-alkyl($C_{12-18}$) dimethylbenzyl ammonium chloride, N-alkyl($C_{14-18}$) dimethyl-benzyl ammonium chloride, N-etetradecyldimethylbenzyl ammonium chloride monohydrate, dimethyl didecyl ammonium chloride, N-alkyl and ($C_{12-14}$)dimethyl 1-napthylmethyl ammonium chloride, trimethylammonium halide, alkyl-trimethylammonium salts and dialkyldimethylammonium salts, lauryl trimethyl ammonium chloride, ethoxylated alkylamidoalkyldialkylammonium salt and/or an ethoxylated trialkyl ammonium salt, dialkylbenzene dialkylammonium chloride, N-didecyldimethyl ammonium chloride, N-tetradecyldimethylbenzyl ammonium, chloride monohydrate, N-alkyl($C_{12-14}$)dimethyl 1-naphthylmethyl ammonium chloride and dodecyldimethylbenzyl ammonium chloride, dialkyl benzenealkyl ammonium chloride, lauryl trimethyl ammonium chloride, alkylbenzyl methyl ammonium chloride, alkyl benzyl dimethyl ammonium bromide, $C_{12}$, $C_{15}$, and $C_{17}$ trimethyl ammonium bromides, dodecylbenzyl triethyl ammonium chloride, poly-diallyldimethylammonium chloride (DADMAC), dimethyl ammonium chlorides, alkyldimethylammonium halogenides, tricetyl methyl ammonium chloride, decyltrimethylammonium bromide, dodecyltriethylammonium bromide, tetradecyltrimethylammonium bromide, methyl trioctylammonium chloride (ALIQUAT 336™), POLYQUAT 10™, tetrabutylammonium bromide, benzyl trimethylammonium bromide, choline esters (such as choline esters of fatty acids), benzalkonium chloride, stearalkonium chloride compounds (such as stearyltrimonium chloride and Di-stearyldimonium chloride), cetyl pyridinium bromide or chloride, halide salts of quaternized polyoxyethylalkylamines, MIRAPOL™ and ALKAQUA™ (Alkaril Chemical Company), alkyl pyridinium salts, amines, such as alkylamines, dialkylamines, alkanolamines, polyethylenepolyamines, N,N-dialkylaminoalkyl acrylates, and vinyl pyridine, amine salts, such as lauryl amine acetate, stearyl amine acetate, alkylpyridinium salt, and alkylimidazolium salt, and amine oxides, imide azolinium salts, protonated quaternary acrylamides, methylated quaternary polymers, such as poly(diallyl dimethylammonium chloride) and poly-(N-methyl vinyl pyridinium chloride), and cationic guar.

An amphiphilic stabilizer utilized with the drug is typically a molecule having a water-soluble (hydrophilic) polar head and a water-insoluble (hydrophobic) organic tail. Examples of amphiphiles include an anionic surfactant, a cationic surfactant, a nonionic surfactant, or a compatible mixture of surfactants. The surfactant also can be an ampholytic or amphoteric surfactant, which have anionic or cationic properties depending upon the pH of the composition.

In one embodiment, the amphiphile can be an anionic surfactant, and in another any anionic surfactant having a hydrophobic moiety, such as a carbon chain including about 2 to about 30 carbon atoms, and in yet another a carbon chain including about 8 to about 18 carbon atoms, and further has a hydrophilic moiety, such as sulfate, sulfonate, carbonate, phosphate, or carboxylate. Often, the hydrophobic carbon chain is etherified, such as with ethylene oxide or propylene oxide, to impart a particular physical property, such as increased water solubility or reduced surface tension to the anionic surfactant.

Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, oxtoxynol or nonoxynol phosphates, taurates, fatty taurides, fatty acid amide polyoxyethylene sulfates, isethionates, or mixtures thereof. Additional anionic surfactants are listed in McCutcheon's Emulsifiers and Detergents, 1993 Annuals, (hereafter McCutcheon's), McCutcheon Division, MC Publishing Co., Glen Rock, N.J., pp. 263-266, incorporated herein by reference.

In one embodiment, the surfactant is selected from the following classes of surfactants: a $C_8$-$C_{18}$ alkyl sulfate, a $C_8$-$C_{18}$ fatty acid salt, a $C_8$-$C_{18}$ alkyl ether sulfate having one or two moles of ethoxylation, a $C_8$-$C_{18}$ alkamine oxide, a $C_8$-$C_{18}$ alkoyl sarcosinate, a $C_8$-$C_{18}$ sulfoacetate, a $C_8$-$C_{18}$ sulfosuccinate, a $C_8$-$C_{18}$ alkyl diphenyl oxide disulfonate, a $C_8$-$C_{18}$ alkyl carbonate, a $C_8$-$C_{18}$ alpha-olefin sulfonate, a methyl ester sulfonate, and mixtures thereof. The $C_8$-$C_{18}$ alkyl group contains eight to sixteen carbon atoms, and can be straight chain (e.g., lauryl) or branched (e.g., 2-ethylhexyl). The cation of the anionic surfactant can be an alkali metal (preferably sodium or potassium), ammonium, $C_1$-$C_4$ alkylammonium (mono-, di-, tri), or $C_1$-$C_3$ alkanolammonium (mono-, di-, tri-).

The amphiphile also can be a nonionic surfactant. Typically, a nonionic surfactant has a hydrophobic base, such as a long chain alkyl group or an alkylated aryl group, and a hydrophilic chain comprising a sufficient number (i.e., 1 to about 30) of ethoxy and/or propoxy moieties. Examples of classes of nonionic surfactants include ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, and mixtures thereof.

Exemplary nonionic surfactants include, but are not limited to, methyl gluceth-10, PEG-20 methyl glucose distearate, PEG-20 methyl glucose sesquistearate, $C_{11}$-$C_{15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof.

Numerous other nonionic surfactants are disclosed in McCutcheon's Detergents and Emulsifiers, 1993 Annuals, published by McCutcheon Division, MC Publishing Co., Glen Rock, N.J., pp. 1-246 and 266-272, in the CTFA International Cosmetic Ingredient Dictionary, Fourth Ed., Cosmetic, Toiletry and Fragrance Association, Washington, D.C. (1991) (hereinafter the CTFA Dictionary) at pp. 1-651, and in the CTFA Handbook, at pp. 86-94, and the Handbook of Pharmaceutical Excipients, published jointly by the American Pharmaceutical Association and The Pharmaceutical Society of Great Britain (The Pharmaceutical Press, 1986), each incorporated herein by reference.

In yet another embodiment, the saturated polyglycolysed glyceride is GELUCIRE®, the glycerol palmitostearate is PRECIROL®, the saturated $C_{12}$ to $C_{22}$ fatty acid esters of polyalcohol is LUBRIFIAN®, and the glyceryl and polyethylene glycol behenate is COMPRITOL®, all of which are distributed by Gattefosse, Saint-Priest, France, are used. GELUCIRE® is composed of saturated polyglycolysed glycerides. PRECIROL® is atomized glycerol palmitostearate made of mono, di and triglycerides of saturated fatty acids $C_{16}$ and $C_{18}$. LUBRIFIANT® is composed of saturated $C_{12}$ to $C_{22}$ fatty acid esters of polyalcohol. COMPRITOL® is composed of glyceryl and polyethylene glycol behenate.

In accordance with one embodiment, if a metal cation is used as the binding agent, calcium, potassium, magnesium, iron, copper, zinc, aluminum, manganese, chromium, cobalt, nickel, and/or sodium may be used. Each of these metal cations are biocompatible. In another embodiment, cations such as zinc or calcium are most used.

In one embodiment, the final dosage form, or FDF, includes the PDS incorporated into the PDS matrix materials to obtain the desired properties of the drug, i.e. improved flow/dispersion, absorption, controlled-release, etc. For inhaled and nasally-delivered FDFs, a measured dose of powder may be packaged without further processing into a capsule, blister package, etc., for delivery using a dry-powder inhaler or insufflator. In one embodiment, the method of orally administering the combination of a drug in a PDS and PDS matrix in a FDF in accordance with this invention includes tablets, capsules, etc. which may be enteric coated to further improve delivery to specific regions of the GI. In another embodiment, an enteric-coated solid dosage form such as a tablet or capsule is used. The formulation can be filled into a hard- or soft-shell capsule or, if the formulation is a liquid, mixed with a suitable carrier to make a free flowing powder and then filled into the capsule or, alternatively, compressed into a pill or tablet. Still other possible dosage forms include microcapsule or beadlet forms mixed with the PDS matrix, which may thereafter be encapsulated in an enteric-coated capsule.

The composition of the FDF of the present invention may further include other materials such as bulking agents, disintegrating agents, anti-adherants and glidants, lubricants, and binding agents. Bulking agents include, but are not limited to, microcrystalline cellulose (e.g., Avicel®, FMC Corp., Emcocel®, Mendell Inc.), mannitol, xylitol, dicalcium phosphate (eg. Emcompress, Mendell Inc.), calcium sulfate (eg. Compactrol, Mendell Inc.), starches, lactose, sucrose (Dipac, Amstar, and Nutab, Ingredient Technology), dextrose (Emdex, Mendell, Inc.), sorbitol, and cellulose powder (Elcema, Degussa, and Solka Floc, Mendell, Inc.). The bulking agent in one embodiment may be present in the composition in an amount of from about 5 wt. % to about 90 wt. %, and in another embodiment from about 10 wt. % to about 50 wt. %.

Disintegrating agents which may be included in the composition include, but are not limited to, microcrystalline cellulose, starches, crospovidone (e.g. Polyplasdone XL, International Specialty Products.), sodium starch glycolate (Explotab, Mendell Inc.), and crosscarmellose sodium (e.g., Ac-Di-Sol, FMC Corp.). The disintegrating agent in one embodiment may be present in the composition in an amount of from about 0.5 wt. % to about 30 wt %, and in another embodiment from about 1 wt. % to about 15 wt. %.

Antiadherants and glidants which may be employed in the composition include, but are not limited to, talc, corn starch, silicon dioxide, sodium lauryl sulfate, and metallic stearates. The antiadherant or glidant in one embodiment may be present in the composition in an amount of from about 0.2 wt. % to about 15 wt. %, and in another embodiment from about 0.5 wt. % to about 5 wt. %.

Lubricants which may be employed in the composition include, but are not limited to, magnesium stearate, calcium stearate, sodium stearate, stearic acid, sodium stearyl fumarate, hydrogenated cotton seed oil (sterotex), talc, and waxes, including but not limited to, beeswax, carnuba wax, cetyl alcohol, glyceryl stearate, glyceryl palmitate, glyceryl behenate, hydrogenated vegetable oils, and stearyl alcohol. The lubricant in one embodiment may be present in an amount of from about 0.2 wt. % to about 20 wt. %, and in another embodiment from about 0.5 wt. % to about 5 wt. %.

Binding agents which may be employed include, but are not limited to, polyvinyl pyrrollidone, starch, methylcellulose, hydroxypropyl methylcellulose, carboxymethyl cellulose, sucrose solution, dextrose solution, acacia, tragacanth and locust bean gum. The binding agent in one embodiment may be present in the composition in an amount of from about 0.2 wt. % to about 10 wt. %, and in another embodiment from about 0.5 wt. % to about 5 wt. %.

A further alternative involves embedding drug within a wax based tablet, by granulation or simply mixing of drug with a wax, such as carnauba wax, microcrystalline wax or commercially available purified fatty acid esters.

Various compositions of the FDF in the present invention may be made by direct compression methods, wet granulation methods, spheronization, or other methods. In the direct compression method, the PDS and other ingredients may be sieved through a stainless steel screen, such as a 40 mesh steel screen. The sieved materials then are charged to a suitable blender, and blended for 10 minutes with an intensifier bar on for 3 minutes, for example. The blend may then be compressed into tablets for oral delivery on a rotary press using appropriate tooling. The compressed tablets may be coated, if desired.

In the wet granulation method, the PDS and other ingredients may be granulated with a granulating fluid (e.g., isopropyl alcohol, ethyl alcohol, and water) in a planetary mixer, high shear mixer, fluidized bed granulator, or other mixers. Binding agents may be contained in the granulating fluid, or may be in the dry mix. The wet granules may be dried in an oven or fluidized bed dryer, and then sieved through a suitable screen to obtain free flowing granules. The resulting granules may be blended with a suitable lubricant and glidant, and the lubricated granules may be packaged into a blister or compressed into tablets on a rotary press using appropriate tooling. If desired, a coating can be applied onto the compressed tablets.

Tablets for oral delivery of drugs of the invention may also optionally include an optional coating layer that may comprise from 0 to about 15% by weight of the tablet composition. The coating layer which is applied over the outer part of the FDF containing the PDS in the inner solid phase embedded therein may comprise any typical coating formulations and will include one or more film-formers or binders, such as a hydrophilic polymer like hydroxypropylmethylcellulose, and/or a hydrophobic polymer like methacrylic acid esters neutral polymer, ethyl cellulose, cellulose acetate, polyvinyl alcohol-maleic anhydride copolymers, β-pinene polymers, glyceryl esters of wood resins and the like, and one or more plasticizers, such as triethyl citrate, diethyl phthalate, propylene glycol, glycerin, butyl phthalate, castor oil and the like. Bulking/disentigrating agents may also be added to the PDS to obtain the desired dispersion/flow properties and/or produce a specific volume for reproducible measuring of the FDF. Specific examples include, but are not limited to, lactose (Pharmatose®, DMV Pharma), mannitol, xylitol, dicalcium phosphate (Emcompress, Mendell Inc.), calcium sulfate (Compactrol, Mendell Inc.), starches, lactose, sucrose (Dipac, Amstar, and Nutab, Ingredient Technology), dextrose (Emdex, Mendell, Inc.), sorbitol, cellulose powder (Elcema, Degussa, and Solka Floc, Mendell, Inc.), microcrystalline cellulose (MCC, Avicel®, FMC Corp.), MCC/colloidal silicon dioxide (PROSOLV SMCC™, Penwest), hydroxypropylmethylcellulose (Methocel™, Dow Chemical), polyvinylpyrrolidone (Kollidon® SR, BASF), agglomerated locust bean gum and xanthan gum (TIMERX™, Penwest), and other agents. The bulking agent in one embodiment may be present in the composition in an amount of from about 1 wt. % to about 90 wt. %, and in another embodiment from about 5 wt. % to about 50 wt. %. Both core tablets as well as coating formulations may contain coloring agents, such as aluminum flakes, and flavoring agents to produce the desired FDF.

Usage of enteric coating materials in the present invention may be used to protect the drug in the PDS from the gastric fluid, i.e. a pH-sensitive cephalosporin or protein, and to achieve optimum delivery to the desired region of the intestine. Other biologically active agents such as enzyme inhibitors or pH-modulating agents may also be included to further protect drugs from degradation, i.e. enzyme inhibitors, pH-modifiers, etc. The enteric coating material is, for the most part, resistant to the gastric fluid and is unaffected by it but dissolves in the intestinal fluid to cause release of the drug. The effectiveness of particular enteric coating materials can be measured using known USP procedures. By way of illustration, suitable enteric coating materials for purposes of this invention include but are not limited to the following: cellulose acetate phthalate, cellulose acetate trimellitate, hydroxypropyl methylcellulose phthalate, hydroxypropyl methylcellulose phthalate succinate, polyvinyl acetate phthalate, methacrylic acid, and methacrylic acid esters. These enteric coating materials may be applied with or without plasticizers, such as acetylated glycerides or diethylphthalate.

In one embodiment, the percentage of enteric coating applied is usually between about 1 and about 10 percent by weight, or more, and in another embodiment from about 2 to about 8 percent by weight, based on the total weight of the unit dosage form, i.e., the total capsule or table weight.

It will be recognized by one of skill in the art that the amount of drug required for therapeutic effect on administration will, of course, vary with the chosen compound and the nature and severity of the condition and the patient undergoing treatment, which is ultimately at the discretion of the physician. Furthermore, the optimal quantity and spacing of individual dosages of a drug will be determined by the nature and extent of the condition being treated, the form, route and site of administration, the particular patient being treated and that such optima can be determined by pharmacokinetic techniques. It will also be appreciated that the optimal course of treatment, that is, the number of doses given, can be ascertained by those skilled in the art using conventional course of treatment determination tests. In many cases very potent drugs may provide the desired effect upon delivery of several milligrams or less, not limiting the use of large volumes of excipients and other ingredients in the FDF. In some cases, drugs must be delivered to the patient in amounts of several hundred milligrams to amounts greater than one gram, once or more daily, in the form of one or more tablets and/or capsules, to provide the desired effect. In one embodiment, the present invention, the drug incorporated into the PDS with other ingredients in the FDF is described which may be greater than 50% drug, and in another embodiment greater than 80% drug, while still providing optimum therapeutic or diagnostic effects.

In another embodiment, a pulmonary dry-powder formulation is prepared incorporating drug particles and excipients of the present invention. Exemplary pulmonary drugs that could be used include glucocorticoids and other localized asthma drugs, as well as drugs and bioactive peptides and proteins for systemic delivery, such as insulin.

Topical drugs that could be used include localized antibiotics, antifungals, and anti-inflammatories. Parenteral drugs that could be used include many currently used suspensions and preparations for sustained or localized release, or simply to reduce hydration and improve shelf-life of protein powders.

In illustrative embodiments, the resulting milled particles may range in size from about 10 or 20 nm in average diameter up to and including about 1 or 2 mm in diameter. In another embodiment, the drug particles may range in size from about 100 or 200 nm in diameter up to and including about 100 to 200 microns in diameter. In other embodiments, drug particles may range in size from about 500 or 600 nm in diameter up to and including about 10 or 15 microns in diameter. By modifying the particular parameters of the drug particle milling/modifying process, particles of slightly larger or smaller average diameter particle sizes, may be obtained.

EXAMPLES

The following examples are included to demonstrate embodiments of the invention. It should be appreciated by those of skill in the art that the techniques disclosed in the examples which follow represent techniques discovered by the inventors to function well in the practice of the invention, and thus can be considered to constitute relevant examples for its practice. However, those of skill in the art should, in light of the present disclosure, appreciate that many changes can be made in the specific embodiments which are disclosed and still obtain a like or similar result without departing from the spirit and scope of the invention.

Example 1

Lactose/2% leucine (100 g) powders were prepared using low-frequency sonication drying according to WO 03/090717. The mixture was allowed to freeze overnight (−5° C., Kenmore Freezer) and then placed in a funnel connected to Bransonic spoon feeder attached to Trost Gem-T jet mill. A liquid and gas nitrogen mixture (from metal liquid nitrogen dewar, Praxair) was adjusted resulting in a flow of 100 to 180 CFM (80 to 100 psi combined input pressure) and a temperature of −2 Celsius above the cyclone read from a TSI Model 4040 Flowmeter. The powder was fed into the mill over 5 minutes and the resulting powder in the cup below the cyclone passed again through the mill three additional passes. The resulting white powder in the cup and bag was obtained with a yield of 92 g, containing particles with a diameter less than 10 microns and highly electrostatic. The particles obtained could be used as a carrier for use in a dry powder inhaler or oral capsule formulation.

Example 2

Spray-dried gentamicin sulfate USP (80 g, Hawkins), inhalation-grade lactose (16 g, Respitose, DMV), sodium chloride (2 g, Fisher), and l-leucine (2 g, Spectrum) was mixed in a turbula mixer (Glen Mills) at room temperature for 10 minutes. The resulting dry mix was then granulated in a shear mixer with water. The wet granulation was then spread into a stainless steel bowl and dried in an oven at 40 Celsius for 2 days. The dried granules were then milled through an 18 mesh (1 mm) screen. The mixture was allowed to freeze overnight (−5 Celsius, Kenmore Freezer) and milled similar to the method of EXAMPLE 1. The powder was fed into the mill over 5 minutes and the resulting powder in the cup below the cyclone passed again through the mill three additional passes. The resulting white powder in the bag was obtained with a yield of >60 g, containing particles with a diameter less than 10 microns and highly electrostatic. The particles obtained could be used as an inhaled antibiotic treatment for respiratory infection.

The resulting inhaled gentamicin formulation was tested for lung delivery in rats. Animals were anesthetized and they received a jugular cannulation to sample blood at different timepoints to measure the release rate and systemic absorption. Gentamicin powders were administered at a dose of 5 mg/kg either IV in a saline solution or intratracheally (IT) diluted in ultra fine lactose. For IT administration animals received a tracheotomy and powders were delivered using the Penn Century insufflator. Blood samples were collected at 0, 10, 30, 60, 90, 120, 180, 240, 300, and 360 minutes in heparinized tubes and gentamicin was measured using an enzyme immunoassay kit (Euro-Diagnostica). While in vitro testing showed a higher respirable fraction following milling, the absorption of milled gentamicin was complete and sustained following delivery to the lungs.

Additional batches were prepared similarly and coated with 0.5 to 1% magnesium stearate, according to the method described in U.S. Pat. No. 6,406,645, to improve the dispersion properties from a dry-powder inhaler (Cyclohaler or similar).

Example 3

Acyclovir, USP (Hawkins), PVP K-30 (ISP), and zinc acetate (Spectrum), powders (80 g, 1:2:5 ratio by mass) were mixed in a turbula mixer (Glen Mills) at room temperature for 10 minutes. Similar to EXAMPLE 1, the mixture was placed in a funnel connected to Bransonic spoon feeder attached to Trost Gem-T jet mill. A liquid and gas nitrogen mixture was adjusted resulting in a pressure of 90 psi (+/−10 psi) in each jet. The powder was fed into the mill over approximately 5 minutes and the resulting powder in the cup below the cyclone passed again through the mill three additional passes. The resulting white powder in the bag was obtained with a yield of >60 g, containing particles with a diameter less than 10 microns and highly electrostatic. The particles obtained could be used to fill capsules or added to a heated propylene glycol/aqueous solution in preparation of a clear hydrogel for topical application.

Example 4

Initial Zn-DTPA simple salt solutions were prepared and lyophilized, producing a hygroscopic mixture not stable at room temperature and humidity (>10% moisture uptake in 24 hours). Zn-DTPA (trisodium zinc diethylenetriaminepentaacetate) were then mixed with (1) hydroxyl-propyl-methylcellulose (HPMC, K100M, Dow), (2) lactose (USP, Hawkins), and (3) silica dioxide (Sipernat 50S, Degussa) and dried using lyophilization. Preparation procedures include (A) mixing ingredients (75 and 90% Zn-DTPA, 1 g total each) into 10 ml DI water and adjusting pH with NaOH, (B) freezing at −20 C, (C) lyophilizing overnight (shelves at room temp), and (D) measuring the moisture uptake (weight change) at room temperature (20-25° C.) and humidity (40-55%) at 1 month. Addition of HPMC, lactose, and $SiO_2$ resulted in <10% at 1 month, and further jet-milled in 6 to 8 g batches (NQ-DTPA) according to the method of EXAMPLE 1.

NQ-DTPA powders were analyzed using a Joel model 6330 Cold-Field Emission Gun Scanning Electron Microscope (SEM) to obtain information on the size, shape, and surface morphology. Characterization was performed at 1-2 KeV in vacuum providing resolutions of 100 to 1,000 times. Comparison of particles were not quantitative, but they appeared to be micron scale and below in size. The particles obtained could be used as an oral or inhaled treatment for radionucleotide chelation, or chelation of iron for cancer therapy.

Example 5

Figure 2:
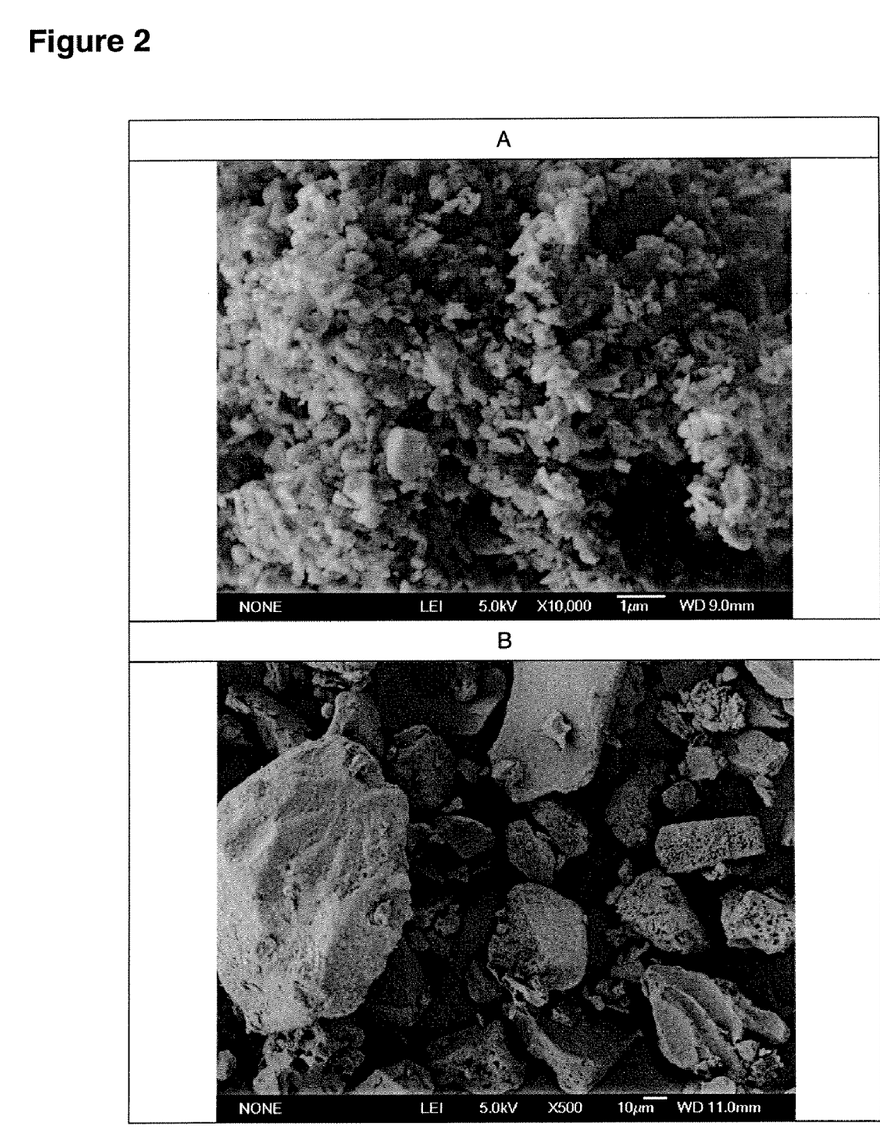
FIG. 2A is a scanning electron micrograph of jet-milled barium glass/5% methacrylic acid copolymer (Eudragit L100, Rohm) nanoparticles at 10,000 times magnification.
FIG. 2B is a scanning electron micrograph of jet-milled loperamide HCl/95% methacrylic acid copolymer microparticles at 500 times magnification.

Pure ball-milled barium glass (barium-aluminum-silicate, 605 nm) and ball-milled barium glass/5% methacrylic acid copolymer (Eudragit L100, Rohm), 50 g batches, were milled in four passes according to EXAMPLE 1, as well as four passes using pressurized air for comparison. Barium glasses are used as fillers in orthodontic adhesive formulations, including light curable preparations, to improve the adherence of orthodontic appliances to the surface of etched human teeth (exhibiting lower polymerization shrinkage). The particle size after three passes each, measured using a Coulter DELSA 440 (PN 6604021) in triplicate against ASTM latex bead standards, was 396-544 nm for the powders milled in nitrogen (92% yield), 474-556 nm for powders milled in pressurized air (30% yield), and 510-700 nm for unmilled barium glass. The particles milled in nitrogen are shown in FIG. 2A. Barium glass nanoparticles could be prepared at high yield using the described invention compared to standard jet milling, which demonstrated poor recovery.

Example 6

Taurine, an anti-oxidant, is a water-soluble compound. Taurine (95%) was mixed with Macol® LA-12 (5%, BASF) in a 1 kg batch and milled according to the method described in EXAMPLE 1. Milled taurine formulations (NQ-TAU) demonstrated improved bioavailability in vivo and weak anti-oxidant activity in vivo following oral administration in transgenic mice who develop α-amyloid deposits. In vivo pharmacokinetics of two different NQ-TAU (NQ1-TAU and NQ2-TAU) formulations were compared in rats, demonstrating an increase in bioavailability over four times (ND2-TAU, 75% BA) compared to unformulated taurine in solution (18% BA). NQ2-TAU was then compared to unformulated TAU in reducing plaque formation in a transgenic Alzheimer's Disease (AD) mouse model after 10 weeks supplementation. Fewer plaques were observed in the group treated with the highest dose (1 g/kg) of NQ2-TAU versus the group treated with the highest dose (1 g/kg) of unformulated TAU, but not when compared to control animals. Oral taurine and other anti-oxidant preparations may be useful in Alzheimers treatments.

Example 7

Oxcarbazepine, an antiepileptic drug marketed as Trileptal® by Novartis, is a white crystalline powder practically insoluble in water. Oxcarbazepine (100%) was milled in 1 kg batches according to the method described in EXAMPLE 1. Powders were recovered at >98% each pass and the particle size after each pass was 2250 nm±190 nm (Pass 1), 524 nm±44 nm (Pass 2), 400 nm±33 nm (Pass 3), and 264 nm±51 nm (Pass 4).

Oxcarbazepine extended release capsule formulations were developed using milled powder (from Pass 4, 300 mg oxcarbazepine per capsule), with 50 mg PEG300 in an extended-release gum base. Formulations were administered orally as a whole 300 mg tablet vs. oxcarbazepine immediate release tablets (Trileptal®) to healthy volunteers. Pharmacokinetic parameters were generated for both oxcarbazepine and the MHD (10-hydroxy-carbazepine) metabolite, which is primarily responsible for oxcarbazepine's pharmacological activity. The capsule formulation from Pass 4 showed a similar concentration time profile to the immediate release formulation for MHD, as well as bioequivalence in fed patients.

Example 8

Another insoluble CNS compound, 2157 (96%, a galanin-3 antagonist, Lundbeck), was mixed with 4% PVP K-30 and milled in 20 g batches similar to EXAMPLE 1. Galanin receptors have been identified as important in memory function both in flies and mammalian systems. Powders were recovered at >75% and the particle size was 652 nm±98 nm by Coulter (similar to EXAMPLE 5), compared to >3 microns unmilled.

Example 9

A mixture of 95% methacrylic acid copolymer (Eudragit L100, Rohm) and 5% loperamide HCl (Spectrum), 20 g batch, was prepared from a 20% chloroform/80% isopropanol (100 ml) solution dried in a stainless steel bowl at 40° C. overnight. Particles were removed, milled initially in a Retsch Grindomix GM 200 Knife Mill for 2 minutes, and then jet-milled in 2 passes similar to EXAMPLE 1. A white powder was obtained with a yield of 5.7 grams, containing particles with a diameter from 50 microns and smaller. The particles appeared slightly clumped and dissolved slowly upon addition of water. The particles are shown in FIG. 2B and appeared 20 to 40 microns in size. The particles obtained could be used in a pH-dependant release oral taste-masked formulation (loperamide base possesses an extremely bitter taste), such as a fast dissolving tablet, for treatment of diarrhea.

Example 10

Bovine serum albumin (BSA) was jet-milled similar to example 1. The particles appeared 5 to 10 microns after a two passes, compared to several hundred microns unmilled, and the molecular weight appeared unchanged measured by MALDI-TOF. Similar peptide/protein formulations could be prepared for stable oral or inhaled preparations.

Example 11

Measles vaccine, EZ strain live attenuated free-dried vaccine (Sii, India), was diluted with 1 ml sterile water. Lactose and other excipients were added and then agitated using the method according to WO 03/090717. Particles were then jet-milled similar to EXAMPLE 1, appearing <10 microns in size after 2 passes, relevant for inhaled administration. Placque-forming units (PFUs) were measured to compare the activity of the measles vaccine preparations. To all the dried samples including the control, formulations were resuspended by vortexing in 5 ml tissue culture media (MEM). From these "neat stocks" (viral suspension in MEM) triplicates of six ten-fold serial dilutions were made in MEM. Then, 180 ml from each dilution and neat stocks were separately inoculated into confluent Vero cells monolayer in 24 well plates, and they were left for ~30 minutes at 37° C./CO$_2$ incubator for adsorption. Subsequently, 1 ml of MEM containing 2% fetal-calf-serum, antibiotics, and 2% carboxymethyl-cellulose were added to each well. After 6 days of infection, the media was removed and the cell monolayers were stained with crystal-violet stain for 30 minutes. The stain was then removed, followed by PBS wash. The plates were dried and the plaques were counted and computed to give PFU/mg. One sample, ND-MEA-7 measured 98.2% activity (213.3 CFU/mg, 150 mg yield) vs. stock vaccine (543.3 CFU/mg, 60 mg). Stable dry-powder formulations may be administered by inhalation or intranasal route for non-invasive mass immunization.

The drug particle milling/modification techniques described herein, and the compositions derived therefrom, are applicable to a wide variety of compositions, including, but not limited to, pharmaceutical compositions for human or veterinary use, biotechnology applications, herbicides, or pesticides. Pharmaceutical compositions include organic and inorganic active compounds, including biologically active peptides, proteins, and nucleic acids. Pharmaceutical compositions of the invention may be delivered by inhalation through the respiratory tract, as well as, orally, parenterally, or transdermally. In the embodiment of an implant, or other slow release formulation, such compositions may be manually placed into a body. Methods of delivery of such compositions are well practiced in the art, and are described, for example, in Modern Pharmaceutics, Second Edition, edited by Gilbert S. Banker and Christopher T. Rhodes, the entire contents of which is hereby incorporated by reference.

REFERENCED DOCUMENTS

All publications and patents cited in this disclosure are incorporated herein by reference in their entirety. To the extent the material incorporated by reference contradicts or is inconsistent with the present specification, the present specification will supersede any such material. The citation of any references herein is not an admission that such references are prior art to the present invention.

U.S. Patents

| | | |
|---|---|---|
| 3,897,010 | July 1975 | Weishaupt |
| 5,145,684 | September 1992 | Liversidge |
| 5,354,562 | October 1994 | Platz |
| 5,747,001 | May 1998 | Wiedmann |
| 5,997,848 | December 1999 | Patton |
| 6,406,745 | June 2002 | Talton |
| 6,592,903 | July 2003 | Ryde |
| 6,835,396 | December 2004 | Brynjelsen |

Foreign Patent Documents

| | | |
|---|---|---|
| WO 03/090717 | April 2002 | Talton |

Other References

Banker and Rhodes, Eds, Modern Pharmaceutics, Marcel Dekker, Inc., New York, 1990.
McCutcheon's Detergents and Emulsifiers, 2006, published by McCutcheon Division, MC Publishing Co., Glen Rock, N.J.
CTFA International Cosmetic Ingredient Dictionary, Fourth Ed., Cosmetic, Toiletry and Fragrance Association, Washington, D.C. (1991) (hereinafter the CTFA Dictionary) at pp. 1-651.
CTFA Handbook at pp. 86-94.
Handbook of Pharmaceutical Excipients, published jointly by the American Pharmaceutical Association and The Pharmaceutical Society of Great Britain (The Pharmaceutical Press, 1986).
Modern Pharmaceutics, Second Edition, edited by Gilbert S. Banker and Christopher T. Rhodes.

While various embodiments of the present invention have been described above, it should be understood that they have been presented by way of example only, and not limitation. The present invention is not limited to the preparation of drug nanoparticles, nor is it limited to a particular drug, solution, or final product. Nor is the present invention limited to a particular scale or batch size. The present invention is not limited to any particular type or design of jet mill. Thus, the breadth and scope of the present invention should not be limited by any of the above-described exemplary embodiments, but should be defined only in accordance with the following claims and their equivalents.

It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

What is claimed is:

1. A method of milling a powder, comprising:
    introducing a powder to be milled into a jet mill impact chamber,
    introducing a cold stream comprising a mixture of cryogenic liquid and a carrier gas into the jet mill impact chamber; and
    milling the powder in the impact chamber of said jet mill in one or more milling passes.

2. The method of claim 1, wherein the milling is a batch operation.

3. The method of claim 2, wherein the one or more milling passes is/are done successively.

4. The method of claim 1, wherein said cryogenic liquid comprises liquid nitrogen.

5. The method of claim 1, wherein said powder comprises one or more disintegrants, dispersion agents, solubilizers, surfactants, sugars, salts, fatty acid permeation enhancers, or drugs.

6. The method of claim 1, wherein said milling is performed in two or more successive milling passes.

7. The method of claim 1, further comprising a shear mixing or grinding step of said powder.

8. The method of claim 1, wherein said powder comprises particles having diameters ranging from about 100 nanometers to about 1 millimeter.

9. The method of claim 1, wherein said milling occurs at a temperature of about 20 degrees Celsius or lower.

10. The method of claim 1, wherein said milling occurs at a temperature of about −100 degrees Celsius to about 20 degrees Celsius.

11. A method of milling a powder, comprising:
    introducing a powder to be milled comprising particles having a diameter ranging from about 100 nanometers to about 1 millimeter into a jet mill impact chamber;
    introducing a cold stream comprising a mixture of liquid nitrogen and a nitrogen gas into the jet mill impact chamber; and
    milling the powder in said jet mill impact chamber in two or more milling passes.

12. The method of claim 11, wherein said milling is a batch operation.

13. The method of claim 12, wherein said two or more milling passes are done successively.

14. A milling apparatus, comprising:
    a cryogenic gas input system;
    a powder feeder;
    a main jet-mill comprising an impact chamber; and
    at least one output port from said jet-mill for collecting said powder;
    wherein said cryogenic gas input system comprises a cryogenic liquid input and a carrier gas input, wherein said cryogenic liquid input and said carrier gas input are in communication to provide a mixture of cryogenic liquid and a carrier gas prior to the introduction of said mixture into said main jet mill impact chamber.

15. The method of claim 1, wherein said milling occurs at a temperature of about 0 degrees Celsius or lower.

16. The method of claim 1, wherein said milling occurs at a temperature of about −100 degrees Celsius to about 0 degrees Celsius.

17. The method of claim 11, wherein said milling occurs at a temperature of about 0 degrees Celsius or lower.

18. The method of claim 11, wherein said milling occurs at a temperature of about −100 degrees Celsius to about 0 degrees Celsius.

* * * * *